Figure 1:
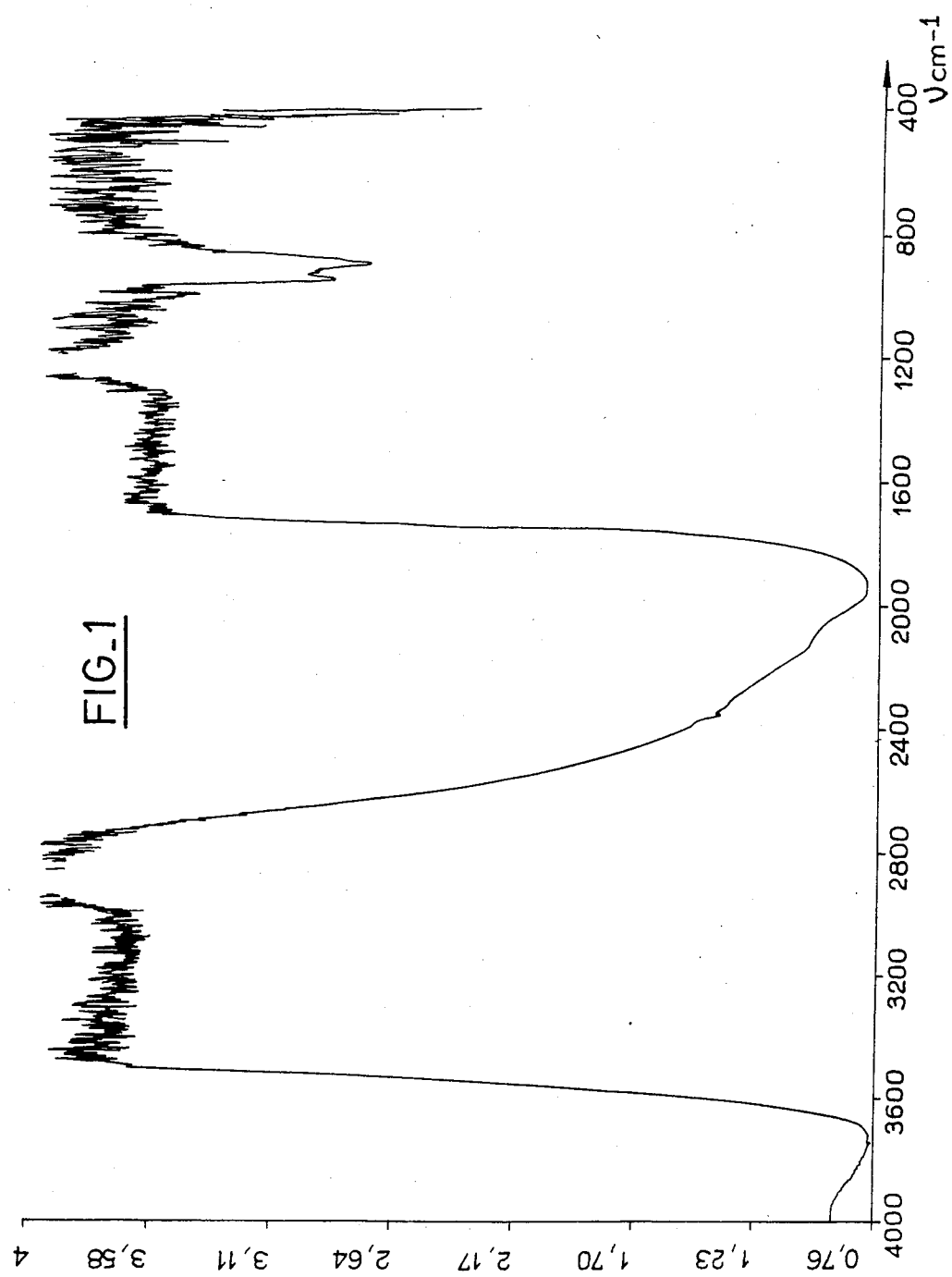

United States Patent [19]

Jaouen et al.

[11] Patent Number: 4,656,142

[45] Date of Patent: Apr. 7, 1987

[54] ORGANOMETALLIC COMPLEXES OF ESTROGENS AND THEIR APPLICATION TO THE DETERMINATION OF HORMONE RECEPTORS

[75] Inventors: Gérard Jaouen; Anne Vessieres, both of La Haye les Roses; Siden Top, Evry, all of France

[73] Assignee: Centre National de la Recherche Scientifique, France

[21] Appl. No.: 534,093

[22] Filed: Sep. 20, 1983

[30] Foreign Application Priority Data

Sep. 23, 1982 [FR] France ................................ 82 16024

[51] Int. Cl.$^4$ .................... G01N 33/566; A61K 31/56
[52] U.S. Cl. .................................. 436/501; 436/817; 514/169
[58] Field of Search .................. 424/12, 238; 514/169; 436/501, 817

[56] References Cited

U.S. PATENT DOCUMENTS 4,205,952  6/1980  Cais ....................................... 424/12
4,466,952  8/1984  Hadd ................................ 260/397.5

OTHER PUBLICATIONS

Chem. Abstracts, vol. 101, No. 23 (1984), Par. 211551x.

*Primary Examiner*—Leonard Schenkman
*Assistant Examiner*—Joseph A. Lipovsky
*Attorney, Agent, or Firm*—Renner, Otto, Boisselle & Lyon

[57] ABSTRACT

The present invention relates to an estrogen complex which consists of an estrogen or an estrogen derivative complexed with an organometallic compound containing at least one free carbonyl ligand, the said estrogen complex containing at least one free hydroxyl radical and no free phenolic hydroxyl radical in the α-position to the site where the organometallic compound is attached.

The complexes according to the invention are useful for the determination of hormone receptors.

12 Claims, 4 Drawing Figures

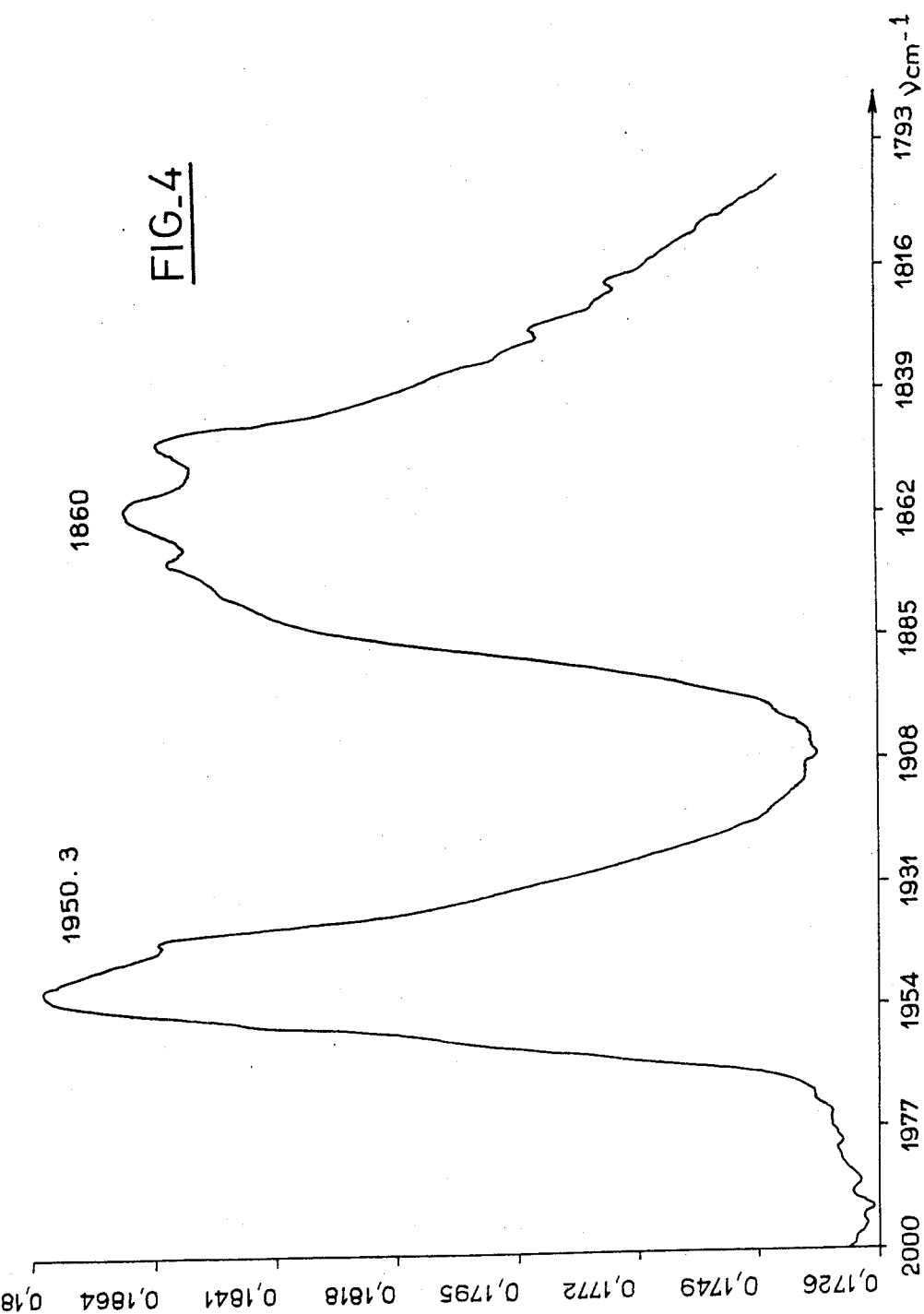
FIG_4

ORGANOMETALLIC COMPLEXES OF ESTROGENS AND THEIR APPLICATION TO THE DETERMINATION OF HORMONE RECEPTORS

FIELD OF THE INVENTION

In a rapidly expanding field such as molecular organometallic chemistry, the main applications have hitherto been confined to stoichiometric and catalytic organic syntheses.

The present invention proposes a new field of application for these derivatives of molecular organometallic chemistry, involving, in particular, the detection and determination of hormone receptors.

PRIOR ART

The primary event which initiates the action of most peptide and steroidal hormones and most medicaments consists in their combination with a specific protein, called a "receptor", located on the cell membrane (in the case of peptide hormones) or in the cytoplasm (in the case of steroidal hormones). Inasmuch as the receptors take part in the action of the biochemical substance or the medicament, it is expected that changes in the concentration of the receptor reflect the state of the illness.

Numerous systems illustrate the correctness of this concept (J. P. Raynaud, T. Ojasoo, M. M. Bouton and D. Philibert, "Drug Design", Volume VIII, Acad. Press (1979), pages 170–214).

For example, in the case of human breast tumors, which is a particular case of hormone-dependent cancers, there are relatively few estrogen receptors in the healthy mammary tissue, but their quantity becomes large in about half of primary breast cancers. A remission rate of 73% has been obtained for patients in which the tumor contains high concentrations of estrogen receptors, whereas a remission rate of only 2% has been observed in the absence thereof (W. L. McGuire, "Hormones and Cancer", Volume 14, Raven Press (1980), pages 337–343).

Until now, essentially for sensitivity reasons, the methods for the determination of receptors have been based on radioisotopic techniques despite their well-known disadvantages (high costs, legal limitations, health risks, limited variety of isotopes which can be used, labeling difficulties, chemical and biochemical instability).

SUMMARY OF THE INVENTION

The present invention proposes to replace the techniques of radioisotopic labeling of estrogens by labeling with the aid of metal carbonyl complexes, using a unique property of metal carbonyl complexes, namely the existence of a $\gamma$— CO band in the region 1,900–2,000 cm$^{-1}$ of the I. R. spectrum, which in fact is just in the "window" left free in proteins.

To do this, the present invention proposes new compounds which can be used, in particular, for detecting and determining hormone receptors and which consist of estrogen complexes containing an estrogen or an estrogen derivative complexed with an organometallic compound possessing at least one free carbonyl ligand, the said estrogen complex containing at least one free hydroxyl radical and no free phenolic hydroxyl radical in the $\alpha$-position to the site where the organometallic compound is attached.

In the definition of the above compounds, it should be noted that:

the existence of a free hydroxyl radical is essential so that the complex obtained has a reasonable degree of recognition for the specific receptor;

the absence of a phenolic hydroxyl radical in the $\alpha$-position to the carbon where the organometallic compound is located, that is to say on the carbon adjacent to the latter, is imposed for reasons of stability, and, finally, the presence of a free carbonyl ligand on the organometallic compound is essential since it is precisely this group which will enable the complex to be detected.

Amongst the estrogens and estrogen derivatives which can be used within the scope of the present invention, the following should be mentioned in particular: estradiol, estrone, 16$\alpha$-hydroxyestrone, estriol and ethynylestradiol, which are hormonal steroids, as well as non-steroidal estrogens, in particular diphenylethane derivatives and stilbene derivatives, such as diethylstilbestrol and hexestrol.

As indicated above, it is possible to use estrogen derivatives; in particular, it is possible, if necessary, to protect some of the hydroxyl groups in order to improve the stability of the compounds, for example by etherification with silane-type derivatives, for example, or by means of $C_1$ to $C_7$ alkoxy groups.

To increase the stability of the compounds, it is also possible to replace a hydroxyl group attached directly to the steroid skeleton by a hydroxylated chain, in particular a preferably $C_1$ to $C_7$ hydroxyalkoxy chain.

If derivatives of steroidal estrogens are employed, it will be preferred to use ethers in the 3-position or 17-position and/or hydroxyalkoxy derivatives in the 3-position.

Within the limits of the general definition, it is possible to use, in the compounds according to the invention, an organometallic compound of any type, in particular organometallic compounds of metals of groups VIa, VIIa or VIII of the Periodic Table, especially chromium, molybdenum, tungsten, manganese, cobalt or nickel, technetium or rhenium.

The ligands of these organometallic compounds can be very varied, in particular CO, CS, CSe CNR$_1$, P(R$_2$, R$_3$, R$_4$) or cyclopentadienyl, R$_1$ being especially an alkyl radical or —COR$_5$ and R$_2$, R$_3$, R$_4$ and R$_5$ being especially substituted or unsubstituted phenyl or phenoxy radicals, substituted or unsubstituted $C_1$ to $C_7$ alkyl or alkoxy radicals or alternatively a halogen atom, it being possible for R$_5$ to be —N(CH$_2$CH$_2$Cl)$_2$.

Amongst these organometallic compounds, the grafts of the following formula must be mentioned more particularly:

M(CO)(L')(L"), in which M is a metal of group VIa and L' and L" are independently ligands mentioned above, for example Cr(CO)$_3$, Cr(CO)$_2$CS, Cr(CO)$_2$CSe, Cr(CO)$_2$CNCO$\phi$, Cr(CO)$_2$P$\phi_3$, Cr(CO)$_2$P(O$\phi$)$_3$, Cr(CO)$_2$PF$_3$, Mo(CO)$_3$ or W(CO)$_3$.

These organometallic compounds are more particularly intended to be attached to an aromatic ring of the estrogen compound.

It is also possible to attach to estrogens or estrogen derivatives, in particular if the latter contains a triple bond, grafts of the formula:

(M'M")(L), in which M' and M" independently represent a metal of group VIa, VIIa or VIII, in particular manganese, cobalt, nickel or molybdenum, and L represents ligands which can be chosen as indicated above for L' and L", for example $Co_2(CO)_6$, $Co(CO)_3NiCp$, $Co(CO)_3Mo(CO)_2Cp$ or $Mn(CO)_4NiCp$ (Cp:cyclopentadienyl).

Amongst the above compounds, those of the formula:

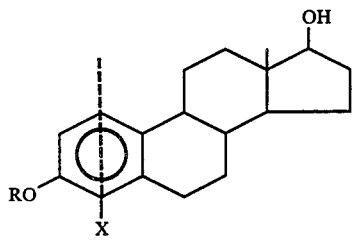

in which R is a protecting radical or a hydroxyalkoxy group and X is an organometallic compound have proved to be of particular interest, especially when R is a silyloxy radical or a radical $HO(CH_2)_n-$, n being between 1 and 7.

Also the following compounds may be useful.

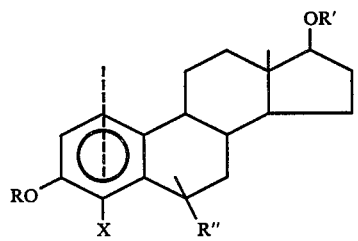

wherein R and R' and X may have the meaning given for R and X in the previous formula and R" is preferably a $HO(CH_2)_n-$ radical, n being between 1 to 7.

The compounds according to the present invention can be prepared by known processes, in particular by reacting the corresponding organometallic derivative with the estrogen compound or the derivative of the estrogen compound. Of course, if necessary, some of the groups of the estrogen compound can be protected, in particular by silylation, and again this can be carried out by known processes.

The present invention also relates to the application of these compounds to the determination of hormone receptors by infrared or Raman spectrography techniques in particular.

In this type of process of detection and determination, the compounds according to the present invention are brought into contact with the samples carrying specific receptors and the presence of the compounds according to the present invention, attached to the hormone receptors, is detected by infrared or Raman spectrography by means of their band having a frequency in the region of 1860 to 2000 $cm^{-1}$.

As will be shown in the examples below, this process makes it possible to detect very small amounts of compounds without resorting to radioactive products, the disadvantages of which are well known.

Furthermore, the process of determination developed in this way falls perfectly within the range of sensitivities required for the present applications, namely, in particular, the detection of primary breast cancers.

This process has the additional advantage of only requiring a very short measurement time (about 1 hour).

The examples below are intended to illustrate the invention.

The solvents are designated as follows: ether=E; petroleum ether=Ep. The NMR spectra were run on a VARIAN EM 360 instrument.

EXAMPLE 1

(a) Synthesis of monosilylated β-estradiol

In a round-bottomed flask purged with nitrogen, 1.2 g ($2.5 \cdot 10^{-2}$ mol) of a 50% dispersion of NaH are suspended in 40 ml of THF. A solution of 5.54 g ($2.10^{-2}$ mol) of estradiol in 40 ml of THF is then added slowly. After half an hour, 3.5 g ($2.33 \cdot 10^{-2}$ mol) of t-BuMe$_2$SiCl are added to the reaction medium in the solid form and the flask is rotated for 3 hours. The mixture is then poured cautiously into iced water, after which the product is extracted with $CH_2Cl_2$. After washing and evaporation of the solvent, 7.86 g of a white solid are obtained. Recrystallization from petroleum ether readily gives 5.7 g of the compound of the formula 1; melting point: 158°, yield: 73%, white crystals.

Analysis: $C_{27}H_{38}O_9CrSi$, found C 74.95; H 9.97; calculated C 74.57; H 9.92;

NMR (CDCl$_3$): ring $\delta=7.2$ d, 6.7. dd, 6.61 d; Me $\delta=0.86$ s; Me$_2$ $\delta=0.23$ s; t-Bu $\delta=1.03$ s.

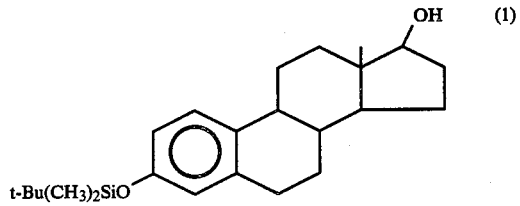

(b) Complex formation with monosilylated β-estradiol 3.2 g ($8.3 \cdot 10^{-3}$ mol) of monosilylated β-estradiol prepared under (a) and 3.7 g ($1.6 \cdot 10^{-2}$ mol) of $Cr(CO)_6$ are placed in a 250 ml round-bottomed flask together with 150 ml of freshly distilled dibutyl ether. The mixture is heated under reflux, under a nitrogen atmosphere, for 8 hours. After evaporation of the solvent, the crude reaction product, which weighs 6.18 g and is a yellow solid, is chromatographed on a column of silica gel 7734 with a 1:1 mixture of E and Ep as the eluent.

The following are isolated:

top fraction: product 2, 1.27 g, yield: 29%, melting point: 220° (E/Ep), yellow crystals.

Analysis: $C_{27}H_{38}O_5CrSi$, found C 61.82; H 7.27; calculated C 62,05; H 7.33;

NMR (CDCl$_3$): ring $\delta=5.76$ d, 5.03 dd, 4.97 d; Me $\delta=0.73$ s; Me$_2$ $\delta=0.20$ s; t-Bu $\delta=0.90$ s;

bottom fraction: product 3, 1.8 g, yield: 41.5%, melting point: 179° (E/Ep), yellow crystals.

Analysis: $C_{27}H_{36}O_5CrSi$, found C 62.00; H 7.30; calculated C 62.05; H 7.33;

NMR (CDCl$_3$): ring $\delta=5.65$ d, 4.96 d, 4.90 dd; Me $\delta=0.83$ s; Me$_2$ $\delta=0.26$ s; t-Bu $\delta=0.96$ s.

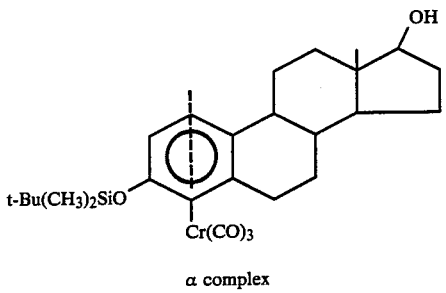

α complex (2)

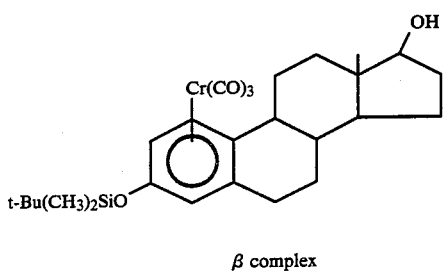

β complex (3)

EXAMPLE 2

(a) α complex of disilylated β-estradiol

The title complex is obtained by silylating compound 2 with excess NaH and excess silane chloride.

Monosilylated estradiol complex 2: 770 mg ($1.4.10^{-3}$ mol), NaH: 600 mg ($1.2.10^{-2}$ mol), t-BuMe$_2$SiCl: 900 mg ($6.10^{-3}$ mol).

After extraction with ether and evaporation of the solvent, 1.9 g of a yellow solid are obtained, which is purified on a column of silica gel 7734 with a 1:7 mixture of E and Ep as the eluent.

0.9 g of product is finally isolated; yield: 96% melting point: 225° (E/Ep), yellow crystals.

Analysis: $C_{33}H_{52}CrO_5Si_2$, found C 62.32; H 8.27; calculated C 62.22; H 8.23;

NMR (CDCl$_3$): ring δ=5.80 d, 5.03 dd, 4.97 d; Me δ=0.73 s; Me$_2$ δ=0.26 s, 0.09 s; t-Bu δ=0.96 s, 0.90

(b) β complex of disilylated β-estradiol

The procedure is identical to that used for its diastereoisomer. Starting from compound 3, the product is obtained with a yield of 93%; melting point: 253° (E/Ep), yellow crystals.

Analysis: $C_{33}H_{52}CrO_5Si_2$, found C 62.23; H 8.21; calculated C 62.22; H 8.23;

NMR (CDCl$_3$): ring δ=5.66 d, 4.94 d, 4.87 dd; Me δ=0.75 s; Me$_2$ δ=0.21 s, −0.05 s; t-Bu δ=0.90 s, 0.83 s.

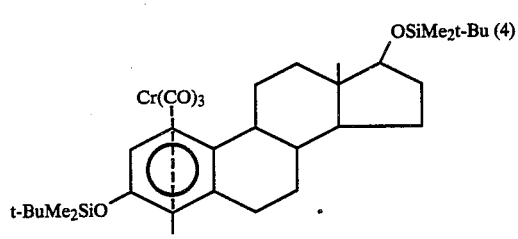

(4)

4′: Cr(CO)$_3$ in the α-position
4″: Cr(CO)$_3$ in the β-position

EXAMPLE 3

Synthesis of compound 5

A solution of 0.52 g ($10^{-3}$ mol) of the α chromium tricarbonyl complex of monosilylated estradiol (compound 2) in 150 ml of benzene and 25 ml of cyclooctene, into which a stream of nitrogen is bubbled, is irradiated for 3 hours. 1 g of P(Ph)$_3$ and 25 ml of CS$_2$ are then added and the mixture is heated at 50° for 1½ hours. After filtration and evaporation, the crude product is chromatographed on a column of Merck silica gel 9385 with a 3:2 mixture of E and Ep as the eluent. 60 mg of the desired product are finally isolated; yield: 11%, melting point: 142° (E/Ep).

NMR (CDCl$_3$): ring δ=5.93 d (1), 5.24 dd (1), 5.11 d (1); Me δ=0.78 s; Me$_2$ δ=0.25 s; t-Bu δ=0.93 s.

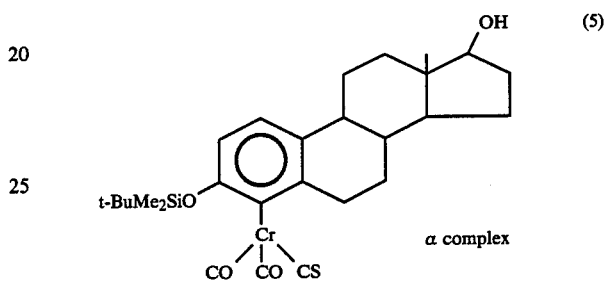

(5) α complex

EXAMPLE 4

(a) Propanol ether derivative of estradiol 1.08 g of estradiol ($4.10^{-3}$ mol) are heated under reflux for 15 hours with 320 mg of sodium hydroxide ($8.10^{-3}$ mol) dissolved in 50 cm$^3$ of acetone, 1.4 g of bromopropanol ($10^{-2}$ mol) are then added and heating is continued for 2 days.

After filtration and evaporation, the residue obtained is redissolved in CH$_2$Cl$_2$. The solution obtained is first washed with water until the pH of the washings is neutral, and then dried over MgSO$_4$, filtered and evaporated. This gives a white solid, which is washed with pentane. A product mass weighing 1.3 g is finally obtained.

Thin layer chromatography (eluent: E/Ep=2/1) shows that the product is pure (yield: 100%).

Recrystallization from ether gives white crystals; melting point: 168°, 900 mg.

NMR (CD$_3$COCD$_3$): ring δ=7.31 d (1), 6.83 dd (1), 6.74 d (1); CH$_3$ δ=0.83 s (3); OCH$_2$ δ=4.14 t (2).

Analysis: $C_{21}H_{30}O_3$, found C 76.05; H 9.17; calculated C 76.32; H 9.15;

Mass spectrum: M+/C=330.2197; $[\alpha]_D^{21}$=70.6 (CH$_2$Cl$_2$, C=0.51).

(b) Complex formation with the propanol ether derivative of estradiol 600 mg of the above compound ($1.8.10^{-3}$ mol), 1.1 g of Cr(CO)$_6$ ($5.10^{-3}$ mol) and 150 cm$^3$ of dibutyl ether are placed in a 250 ml round-bottomed flask. The mixture is heated under reflux for 6 hours. The solution becomes yellow and clear.

After evaporation, 1.24 g of a yellow oil containing several products are obtained.

Chromatography on thick plates of silica gel 7731 with a 2:3 mixture of THF and Ep as the eluent makes makes it possible to isolate two products:

at the top: compound 6, α complex, 270 mg, yield: 32%, yellow solid. Crystallization from E/Ep gives yellow crystals; melting point: 130°.

NMR (CD₃COCD₃): ring δ=6.08 d (1), 5.40 dd (1), 5.34 d (1); CH₃ δ=0.67 s (3); OCH₂ δ=4.0 t (2). $[\alpha]_D^{21}$ =41.7 (CH₂Cl₂, C=1.08). Mass spectrum: 466=M⁺, 382=M⁺−3 CO, 330=M⁺−Cr(CO)₃.

Analysis: $C_{24}H_{30}O_6Cr$, found C 61.30; H 6.68; calculated C 61.79; H 6.48;

at the bottom: compound 7, β complex, 210 mg, yield: 25%, yellow solid. Crystallization from E/Ep gives yellow crystals; melting point: 157°.

NMR (CD₃COCDhd 3): ring δ=6.00 d (1), 5.31 d (1), 5.23 dd (1); CH₃ δ=0.78 s (3), OCH₂ δ=4.04 t (2) $[\alpha]_D^{21}$ =70.0 (CH₂Cl₂, C=1.08). Mass spectrum: 466=M⁺, 382=M⁺−3 CO, 330=M⁺−Cr(CO)₃.

Analysis: $C_{24}H_{30}O_6Cr$, found C 61.84; H 6.60; calculated C 61.79; H 6.48;

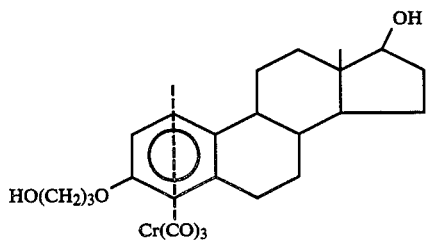

6: Cr(CO)₃ in the α-position
7: Cr(CO)₃ in the β-position

EXAMPLE 5

(Ethynylestradiol)Co₂(CO)₆

Under an argon atmosphere, a solution of 0.6 g of ethynylestradiol (2.10⁻³ mol) in 20 ml of anhydrous ether is added slowly to a solution of 1.05 g of Co₂(CO)₈ (3.10⁻³ mol) in 10 ml of ether. The reaction is left to proceed for 1 hour, the mixture is then filtered and the solvent is evaporated off. The crude product obtained is purified on a column of Merck silica gel 8395 with a 1:1 mixture of E and Ep as the eluent. 1 g of the desired product, which is a blood-red solid, is finally obtained. It is difficult to assign an exact melting point because the product decomposes.

NMR (CDCl₃): ring δ=6.63 d (1), 6.70 dd (1), 7.23 d (1); 3—OH δ=6.21 s (1); CH₃ δ=1.1 (3).

Analysis: $C_{26}H_{24}Co_2O_8$, found C 53.80; H 4.61; Co 19.70; calculated C 53.62; H 4.15; Co 20.24.

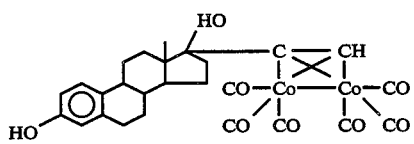

(8)

EXAMPLE 6

Preparation on 6-hydromethyl derivative of 3-benzyloxy 17 βt.butyldimethylsiloxy estradiol tricarbonyl chromium.

The product is prepared according to the following scheme.

The suitably protected 3-benzyloxy 17 β-t.butyldimethyl siloxy estradiol tricarbonyl chromium α 14 and, β 15 derivatives were prepared as follows. Estradiol 11 was complexed by heating with Cr(CO)₆ in dibutyl ether. The mixture of the two Cr(CO)₃ estradiol α and β diastereomers 12 and 13 was rapidly treated with NaH and C₆H₅CH₂Br. The two 3-benzyloxy estradiol Cr(CO)₃ complexes were separated on a silical gel column (eluent:ether/petroleum ether:2/1). Each diastereomer was then treated with NaH and tBuMe₂SiCl to give the products 14 and 15 in 45% yield (ratio: 14/15=56/44 based on isolated complexes). The identification of the diastereomers 14 and 15 has been ascertained by chemical correlation with 3-t.butyl-dimethyl siloxy estradiol Cr(CO)₂CS "α" for which a X-ray structural analysis has been carried out.

The diastereomers are reacted separately with (Me₃-Si)₂NHa to avoid removal of the protecting groups in the 3- and 17-positions and formaldehyd in OMSO. Compounds 14 led to complex 16 (56% yield in isolated product) (mp. 170°) with the CH₂OH group exclusively in the 6 position on the hormone skeleton and anti with respect to the Cr(CO)₃ moiety. A similar regio- and stereospecificity resulted from the reaction of the β diastereomer 15 giving rise to 17 (m.p. 188° C.) in 62% yield.

Products such as 16 and 17 might be valuable precursors in current endocrinology problems such as designed fixation of cytotoxic groups, γ-emitting estrogens and affinity markers (17).

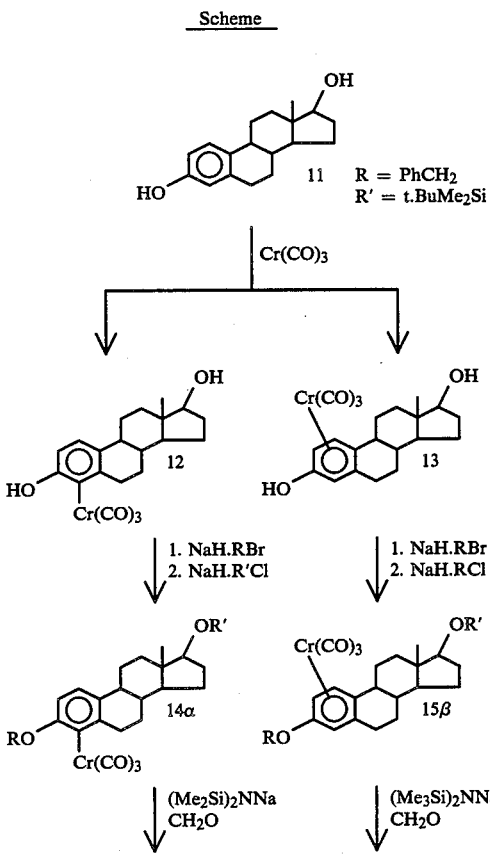

Scheme

-continued
Scheme

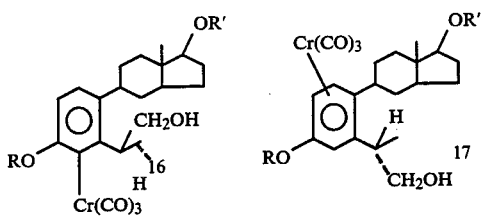

EXAMPLE 7

Detection of hormone receptors using the compounds according to the invention

Various compounds according to the present invention were tested for their ability to compete with estradiol, by means of log/logit curves, as described in Rao et al., Endocrinology, 92, 1229 (1973).

The results are collated in Table I below:

TABLE I

| Compound | RBA (%) |
|---|---|
| estradiol | 100 |
| ethynylestradiol | 71.4 |
| 1 | 11 |
| 2 | 1.05 |
| 3 | 0.36 |
| 4' | no competition |
| 4'' | no competition |
| 5 | 1.5 |
| 6 | 28 |
| 7 | 1.2 |
| 8 | 3.5 |

It must be point out that the further the RBA value (relative binding affinity) is from 100, the lower the competitiveness of the steroid tested. As a concrete example, it should be noted that a medicament as widely used as tamoxifen (Novaldex) has an RBA of 3%.

On looking at this table, it is found that labeling with an organometallic moiety reduces the competitiveness of the hormone modified in this way.

However, with the exception of compound 3, the compounds according to the invention retain the ability to recognize the receptor to an extent which is totally compatible with the use of these products for analytical purposes.

These complexes of the invention are stable in the solid state and can be kept without difficulty in a non-oxidizing medium.

However, the presence of a phenolic hydroxyl group adjacent to an organometallic group is incompatible with the stability of the product, which rapidly decomposes. In this respect, it should be noted that a compound of the same type as those of the invention has been described by G. Pouskouleli, I. S. Butler and J. P. Hickey, J. Inorg. Nucl. Chem., 42, 1659–1662 (1980), but this is the very case of a compound having a phenol group adjacent to the site where the organometallic compound is attached, which makes this compound unstable.

This table shows that, to obtain a good degree of competitiveness, it is necessary to keep hydroxylated groups in the 3-position or 17-position in these products—for example, compounds 4' and 4'' do not exhibit any competition; it is necessary to find solutions which reconcile the two essential requirements above.

As shown by the table, it is firstly possible to carry out the complex formation far away from the phenolic hydroxyl group, for example in the 17α-position as in compound 8.

It is also possible to protect the group in the 3-position by esterification, for example as in compounds 2 and 3, while at the same time keeping the hydroxyl group in the 17-position free.

Finally, it is possible as it were to "move away" the free hydroxyl group in the 3-position by grafting a hydroxyalkoxy radical in this position, as in products 6 and 7.

The most spectacular result is provided by product 6 (RBA: 28%), in which the grafting of a $(CH_2)_3OH$ chain in the 3-position, in conjunction with complex formation on the α side with the $Cr(CO)_3$ group, offers an excellent solution to the problem.

EXAMPLE 8

Detection of a specific estradiol receptor

The samples used in this example were prepared from uterine cytosols of ewes, partially purified by precipitation with 35% ammonium sulfate solution, this process having the dual advantage of reducing the inteference absorbance in the spectral region to be studied and of removing the majority of the non-binding protein associations with the hormone (J. Katznellenbogen et al., "Cytotoxic estrogens in Hormone Receptive Tumors", Acad. Press. London (1980), pages 3–38.)

The samples intended for study by I. R. were prepared using the technique of precipitation with protamine sulfate (A. W. Steggles and R. J. B. King, J. Biochem. 118, 695–701 (1970)), this yielding a white powder which can be used without further treatment.

The attached figures make it possible to understand the applications of the compounds according to the invention.

FIG. 1

I. R. spectrum of the proteins present in the ewe cytosol, purified and treated as specified above. Attention is drawn to the remarkable "window" in the region of 1950 cm$^{-1}$ and the low absorbance at this point. The remainder of the spectral region is characterized by the presence of broad unresolved absorption peaks (maxima off the scale in the present case for greater clarity). The spectrum and those which follow were obtained using an F. T. Nicolet 6000c I. R. instrument, and the weighed and compressed solid sample is simply carried by micropellets. If the estradiol receptor protein is present in the sample studied, only one labeled ligand resonating intensely and specifically at about 1900 cm$^{-1}$ will enable it to be detected.

FIG. 2

I. R. spectrum of the modified hormone 2 in solution. The two intense γ—CO bands of the $A^1$ and E modes respectively are seen at 1959.6 cm$^{-1}$ and 1876.4 cm$^{-1}$. This product, which has a moderate degree of competitiveness, was used in the remainder of the experiment reported here.

FIG. 3

The same sample as that of FIG. 1, but treated with the hormone 2. The two peaks are seen below 2000 cm$^{-1}$. This region has been enlarged for greater clarity. It should be noted that some estradiol receptor is indeed present in the mixture of proteins studied and that it is detectable by I. R. using modified hormones. Because of the concentrations of receptor, a more intense manifestation of its presence is not expected at this level.

FIG. 4

Figure 2:
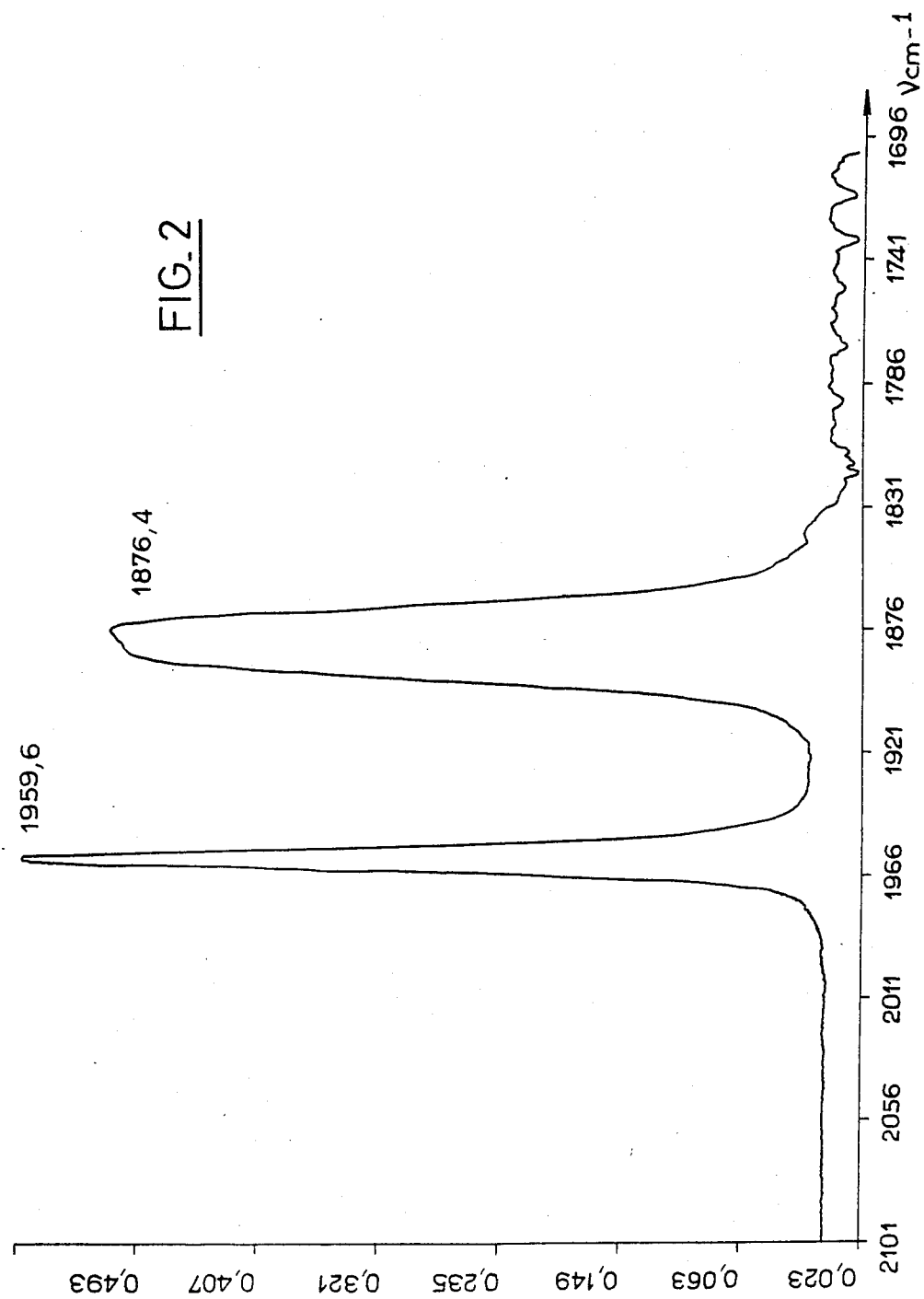
Figure 3:
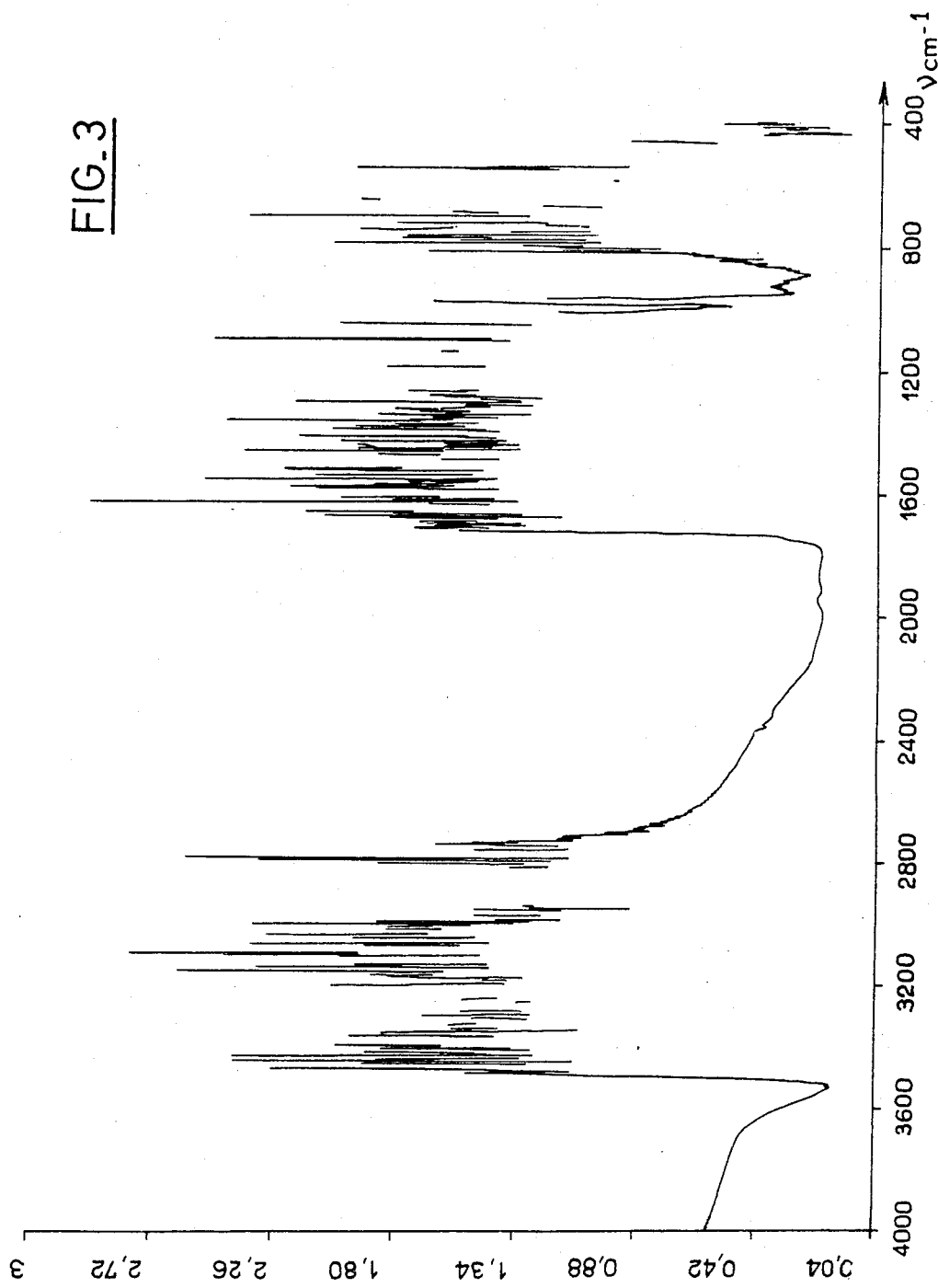

Same sample as that of FIG. 3, obtained after subtraction of the blank (FIG. 1). The result is sufficiently spectacular (compare with the hormone in solution: FIG. 2) not to need any comment.

It should be added that 51 fentomol of receptor per mg of protein were detected here, which represents a totally normal level in cancerology. Below 10 fm/mg of protein, the determination is considered as ER$^-$ (sample threshold under consideration), while levels in excess of 100 fm/mg of protein are common. This technique is therefore within the range of sensitivities required for these delicate analyses.

As a concrete example, it should be noted that $10^{-10}$ g of metal was detected here without difficulty (the limit has not been specified), whereas, by atomic absportion, an amount of less than $10^{-6}$ g of metal cannot be detected, even with very stringent precautions. Furthermore, the typical morphology of the curve (characteristic of a C$_{3v}$ symmetry; the slight splitting is due to the spectrum of the solid) constitutes a measure for guarding against possible artifacts. Finally, the presence of chromium in the sample was confirmed by means of independent neutron activation experiments.

What is claimed is:

1. A process for determining hormone receptors comprising the steps of:
   (1) contacting samples carrying specific receptors with an estrogen complex which comprises an estrogen or an estrogen derivative complexed with an organometallic compound containing at least one free carbonyl ligand, said estrogen complex containing at least one free hydroxyl radical and no free phenolic hydroxyl radical in the alpha-position to the site where the organometallic compound is attached; and
   (2) determining the presence of said compound attached to said receptor by using spectography by means of their band having a frequency in the range of 1860 to 2000 cm$^{-1}$.

2. A process as in claim 1 wherein the type of spectrography used in infrared or Raman spectrography.

3. The process of claim 1 wherein the estrogen is selected from estradiol, estrone, 16 alpha-hydroxyestrone, estriol, ethynylestradiol, diethylstilbestrol, hexestrol or derivatives thereof.

4. The process of claim 3 wherein the derivatives of the steroidal estrogens are ethers in the 3-position or 17-position and/or hydroxy-alkoxy derivatives in the 3-position.

5. The process of claim 3 wherein said organometallic compound is a compound of a metal from Group VIa, VIIa or VIII of the Periodic Table.

6. The process of claim 5 wherein said organometallic compound is a compound of one or more metals selected from chromium, molybdenum, tungsten, manganese, cobalt, nickel, technetium or rhenium.

7. The process of claim 5 wherein said ligand of the metal of said organometallic compound is selected from CO, CS, CSe, CNR$_1$, P(R$_2$,R$_3$,R$_4$) and cyclopentadienyl, R$_1$ being an alkyl radical or —COR$_5$, and R$_2$, R$_3$, R$_4$ and R$_5$ being selected from substituted or unsubstituted phenyl or phenoxy radicals and substituted or unsubstituted alkyl or alkoxy radicals and halogen atoms.

8. The process of claim 7 wherein said organometallic compound is selected from Cr(CO)$_3$, Cr(CO)$_2$CS, Cr(CO)$_2$CSe or Co$_2$(CO)$_6$.

9. The process of claim 1 wherein said estrogen complex is represented by the formula

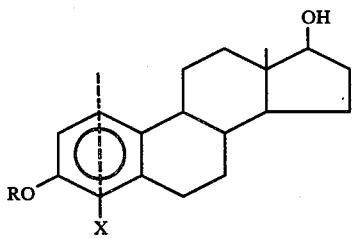

in which R is a protecting group or a hydroxyalkoxy group and X is a complexing organometallic compound of a metal of Group VIa, VIIa or VIII of the Periodic Table.

10. The process of claim 9 wherein X is the radical Cr(CO)$_3$, Cr(CO)$_2$CS or Cr(CO)$_2$CSe, and R is the radical HO(CH$_2$)$_n$—, n being between 1 and 7.

11. The process of claim 1 wherein said estrogen complex is represented by the formula

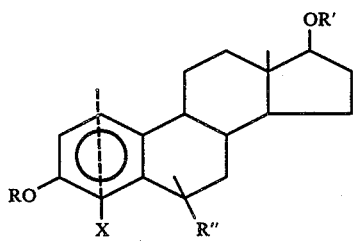

in which R and R' are protecting groups or hydroxyalkoxy groups, X is a complexing organometallic compound of a metal of Group VIa, VIIa or VIII of the periodic Table and R" is a hydroxyalkyl.

12. The process of claim 11 wherein X is the radical Cr(CO)$_3$, Cr(CO)$_2$CS or Cr(CO)$_2$CSe, and R is the radical HO(CH$_2$)$_n$—, n being between 1 and 7.

* * * * *